US008845735B2

(12) United States Patent
Razian et al.

(10) Patent No.: US 8,845,735 B2
(45) Date of Patent: Sep. 30, 2014

(54) SYSTEM FOR REPLACING AN INTERVERTEBRAL DISC

(75) Inventors: Hassan Razian, L'Hay les Roses (FR); Sam Razian, L'Hay les Roses (FR)

(73) Assignee: Hassan Razian, L'Hay-les-Roses (FR)

( * ) Notice: Subject to any disclaimer, the term of this patent is extended or adjusted under 35 U.S.C. 154(b) by 219 days.

(21) Appl. No.: 13/639,118

(22) PCT Filed: Apr. 5, 2011

(86) PCT No.: PCT/FR2011/000197
§ 371 (c)(1), (2), (4) Date: Oct. 3, 2012

(87) PCT Pub. No.: WO2011/124787
PCT Pub. Date: Oct. 13, 2011

(65) Prior Publication Data
US 2013/0023997 A1 Jan. 24, 2013

(30) Foreign Application Priority Data

Apr. 6, 2010 (FR) ...................................... 10 01398

(51) Int. Cl.
*A61F 2/44* (2006.01)
*A61F 2/46* (2006.01)
*A61F 2/30* (2006.01)
*A61F 2/28* (2006.01)

(52) U.S. Cl.
CPC ..... *A61F 2/4611* (2013.01); *A61F 2002/30604* (2013.01); *A61F 2002/30131* (2013.01); *A61F 2002/30538* (2013.01); *A61F 2002/4627* (2013.01); *A61F 2002/30387* (2013.01); *A61F 2250/0006* (2013.01); *A61F 2/4465* (2013.01); *A61F 2230/0013* (2013.01); *A61F 2002/448* (2013.01); *A61F 2/442* (2013.01); *A61F 2220/0025* (2013.01); *A61F 2002/30133* (2013.01); *A61F 2002/2835* (2013.01); *A61F 2002/4475* (2013.01); *A61F 2230/0015* (2013.01)

USPC .......................................... 623/17.16; 606/99

(58) Field of Classification Search
USPC ........................................................ 623/17.16
See application file for complete search history.

(56) References Cited

U.S. PATENT DOCUMENTS 8,500,747 B2 * 8/2013 DeRidder et al. ............... 606/99
8,696,681 B2 * 4/2014 Harris et al. .................... 606/99
(Continued)

FOREIGN PATENT DOCUMENTS

FR          2861582          5/2005
FR          2914842          10/2008
(Continued)

OTHER PUBLICATIONS

International Search Report dated Aug. 23, 2011, corresponding to PCT/FR2011/000197.

*Primary Examiner* — Andrew Yang
*Assistant Examiner* — Olivia C Chang
(74) *Attorney, Agent, or Firm* — Young & Thompson

(57) ABSTRACT

System for replacing a disk between two vertebrae includes an intervertebral cage having an oblong body including at least two portions and separated by a gap extending along a curved axis and opening out through an opening at a first end of the body, and at least one introducer guide rod, a curved longitudinal core having cross-sections substantially complementary to the cross-sections of the gap so as to enable the core and the two portions of the body to slide relative to one another, elements for mounting a first end of the core to co-operate with an end of the guide rod so that the curved core projects from the end, and a push rod mounted to move relative to the guide rod so as to come into contact via one end against the end of the body in order to push the body in translation relative to the core.

13 Claims, 5 Drawing Sheets

(56) References Cited

U.S. PATENT DOCUMENTS

| | | |
|---|---|---|
| 2005/0027360 A1 | 2/2005 | Webb et al. |
| 2005/0096745 A1 | 5/2005 | Andre et al. |
| 2006/0235426 A1* | 10/2006 | Lim et al. .................. 606/99 |
| 2008/0009880 A1* | 1/2008 | Warnick et al. ............ 606/99 |
| 2008/0221694 A1 | 9/2008 | Warnick et al. |
| 2008/0249622 A1* | 10/2008 | Gray .................... 623/17.11 |
| 2010/0318189 A1* | 12/2010 | Edie et al. ............... 623/17.12 |
| 2012/0277866 A1* | 11/2012 | Kalluri et al. ........... 623/17.16 |
| 2012/0310356 A1* | 12/2012 | Davis et al. ............. 623/17.16 |

FOREIGN PATENT DOCUMENTS

| | | |
|---|---|---|
| WO | 00/44288 | 8/2000 |
| WO | 2008/016598 | 2/2008 |

* cited by examiner

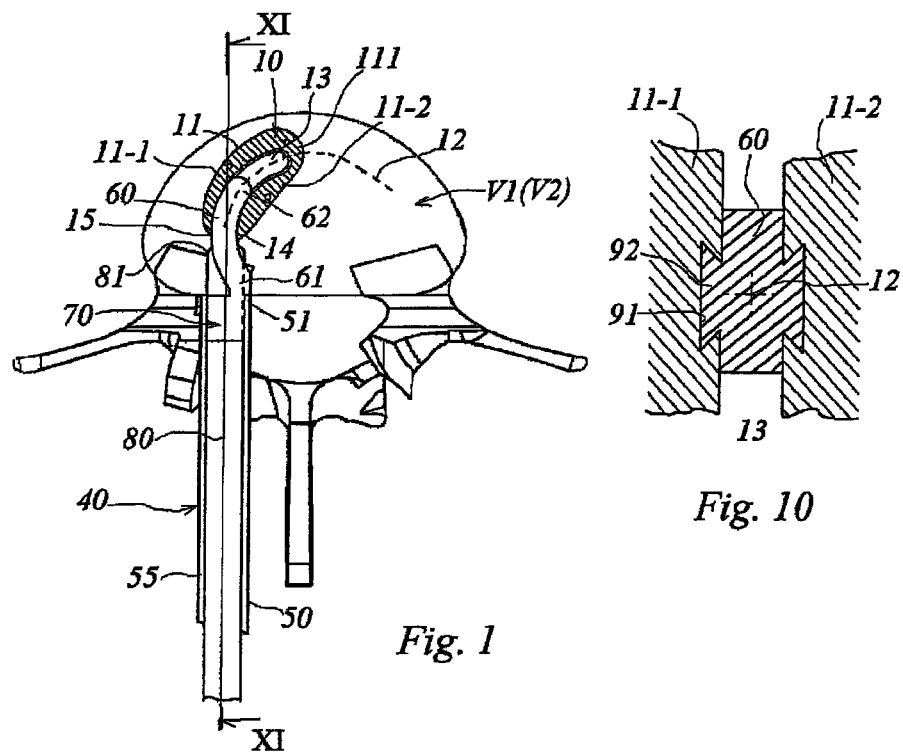
Fig. 1
Fig. 10
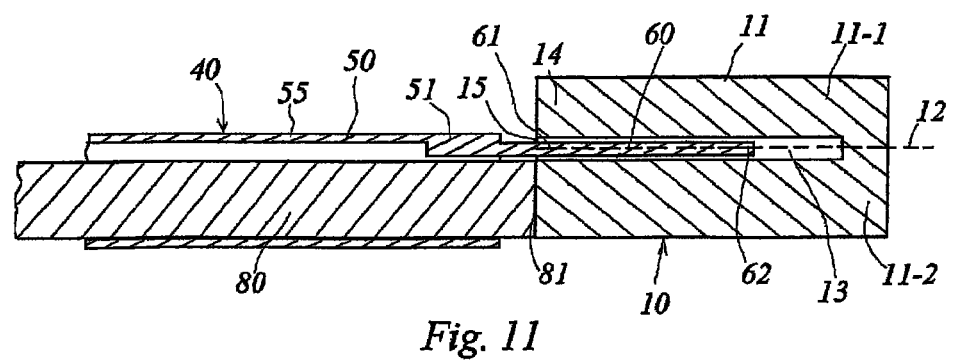
Fig. 11

SYSTEM FOR REPLACING AN INTERVERTEBRAL DISC

FIELD OF THE INVENTION

The present invention relates to systems for replacing an intervertebral disk.

BACKGROUND OF THE INVENTION

Depending on the damage suffered by a spinal column, it is known that practitioners need to perform two kinds of surgical intervention.

When the damage relates only to an intervertebral disk and the two consecutive vertebrae on either side of the disk are in good condition, the practitioner can opt to replace the disk with a prosthesis that is functionally substantially equivalent to the original disk, i.e. it leaves the two vertebrae with freedom to move relative to each other in movements of rotation and/or translation.

In contrast, when the damage is more severe, the practitioner may decide to secure the two consecutive vertebrae to each other by osteosynthesis. To do this, the intervertebral disk is partially or completely destroyed and replaced by an intersomatic cage that is generally associated with an element that encourages osteosynthesis, e.g. a bone graft.

Intersomatic cages are implantable essentially via two approaches, a so-called "anterior" approach and a so-called "posterior" approach, each of these approaches having respective advantages and drawbacks.

Nevertheless, it would appear to be obvious that implanting via the posterior approach is more normal, since the path used by the practitioner for performing the surgery is relatively short. However it is also very tricky, since this path passes very close to elements that are essential for the patient's life, namely the spinal cord and the two nerves that serve in particular to control the patient's movements.

That is why certain practitioners sometimes opt for the "anterior" approach which involves performing surgery over a path that is much longer, but that, in theory, is less dangerous for the patient. In contrast, the time required for surgery is longer when using the posterior approach, and that can present drawbacks for the patient's health and recovery.

Numerous systems have thus been made for replacing a disk between two consecutive vertebrae that enables implantation to be performed in particular via the posterior approach.

By way of example, such systems are described and shown in US 2005/0027360, WO 2008/016598, and WO 00/44288. Nevertheless, those systems are relatively complex, bulky, and difficult to use.

The Applicant has also made such systems, e.g. the system described in FR-A-2 914 842.

SUMMARY OF THE INVENTION

Nevertheless, an object of the present invention is to provide a system for replacing a disk between two consecutive vertebrae that enables implantation to take place via the posterior approach, and that is simpler in structure, therefore being more compact and easier to use than prior art systems in this field, e.g. the systems defined in the above-mentioned documents.

More precisely, the invention provides a system for replacing a disk between two consecutive vertebrae, the system comprising at least one intervertebral cage and an introducer guide for introducing said intervertebral cage between the two vertebrae, and being characterized by the facts that:

the intervertebral cage is constituted by an oblong body defined between two substantially parallel opposite faces, said oblong body comprising at least two portions separated by a gap, said gap being defined along a curved axis contained in a midplane substantially parallel to the planes of the opposite faces and opening out via an opening at a first end of the oblong body between said two portions of said oblong body; and the introducer guide is constituted by at least:
 a guide rod;
 a curved longitudinal core of cross-sections that are substantially complementary to the cross-sections of said space, so as to enable said curved core to slide relative to the two portions of said oblong body;
 means for mounting a first end of said curved core to co-operate with a first end of said guide rod in such a manner that said curved core projects from said first end of said guide rod; and
 a push rod mounted to move relative to said guide rod in such a manner as to be suitable for coming into contact via one of its ends against the first end of the oblong body in order to push said oblong body in translation relative to said curved core.

BRIEF DESCRIPTION OF THE DRAWINGS

Other characteristics and advantages of the invention appear from the following description given with reference to the accompanying drawings by way of non-limiting illustration, in which:

FIG. 1 is a highly diagrammatic view of an embodiment of the system of the invention for replacing a disk between two consecutive vertebrae;

FIGS. 10 and 11 are two diagrammatic section views showing the system of the invention and serving to explain its structure, FIG. 10 being a fragmentary section of the system on X-X in FIG. 7, and FIG. 11 showing a section of the system on XI-XI of FIG. 1.

DETAILED DESCRIPTION OF THE INVENTION

Figure 2:
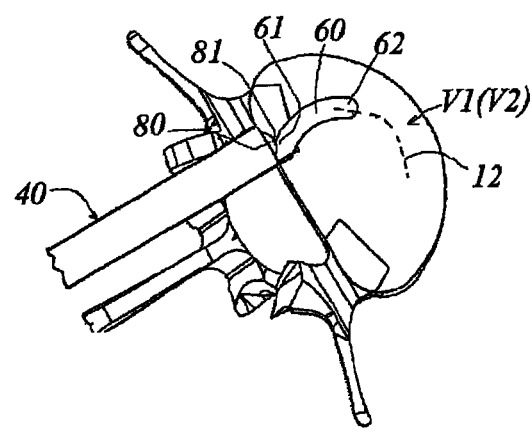
FIGS. 2 to 5 show various configurations of the system of the invention in the embodiment of FIG. 1, FIG. 2 showing the system without its "cage" element, FIG. 3 showing the system in its initial configuration, the cage already being interposed between two vertebrae, FIG. 4 showing the system in an intermediate configuration, the cage being positioned in a state close to its final position, and FIG. 5 showing the system with the cage in its final state.

It is specified that the figures show essentially two embodiments of the subject matter of the invention, but that other embodiments can exist that satisfy the definition of the invention.

With reference more particularly to FIG. 1, the present invention relates to a system for replacing a disk between two consecutive vertebrae V1 and V2 (only one visible in the figures), the system comprising at least one intervertebral cage 10 and an introducer guide 40 for introducing the intervertebral cage between the two vertebrae.

In the meaning of the present invention, the term "intervertebral cage" 10 is used to mean both an intervertebral cage proper in the terminology of persons skilled in the art, and also any other body suitable for being introduced between two vertebrae, which body may be in one or more parts, and regardless of its or their functions, e.g. a disk prosthesis. The term "intervertebral cage" is used herein merely to simplify and facilitate understanding of the invention and its description.

According to an essential characteristic of the invention, the intervertebral cage 10 is constituted by an oblong body 11 defined between two substantially-plane opposite faces, the oblong body having at least two portions 11-1 and 11-2 that are separated by a gap 13, the gap extending along a curved axis 12 contained in a midplane substantially parallel to the planes of the opposite faces and opening out via an opening 15 at a first end 14 of the oblong body 11 between the two portions 11-1 and 11-2 of the oblong body.

According to another characteristic of the invention, the introducer guide 40 is constituted by at least one guide rod 50, an advantageous embodiment of which is described below, and by a curved longitudinal core 60 of cross-sections that are substantially complementary to the cross-sections of the gap 13 so as to enable the curved core to slide relative to the two portions 11-1 and 11-2 of the oblong body 11.

Two embodiments of this curved core 60 are described below respectively with reference to FIGS. 2 to 5 and with reference to FIGS. 6 to 9.

There are also provided both means 70 for mounting a first end 61 of the curved core 60 in co-operation with a first end 51 of the guide rod 50 so that the curved core projects relative to said first end 51 of the guide rod, and also a push rod 80 mounted to move relative to the guide rod 50 in such a manner as to be suitable for coming into contact via one of its ends 81 against the first end 18 of the oblong body 11 so as to push the oblong body in translation relative to the curved core 60.

In a first possible embodiment, the oblong body 11 is constituted by a single part 111 and the gap 13 is constituted by a hole made in the single part substantially along the above-defined curved axis 12.

It is also advantageous for this hole to open out into both substantially plane opposite faces of the intervertebral cage 10 so as to make it possible to place a bone graft or the like therein, where appropriate.

Advantageously, and as shown, the single part 111 is substantially in the shape of a kidney bean, or the like, however its opposite faces are substantially plane.

Under such circumstances, and as shown in FIGS. 1 to 5, all of the cross-sections of the curved core 60, as defined in planes perpendicular to the curved axis 12, are substantially identical to one another.

In a first option, in order to prevent the single part 111 from being capable of pivoting at least in part about the curved core 60, but while nevertheless allowing this single part 111 to slide relative to the curved core, it is most preferable for the cross-sections of said curved core 60, as defined in planes perpendicular to the curved axis 12, to be polygonal in shape. For example, in the embodiment shown in FIG. 10, the cross-section of the curved core is of rectangular shape, however other shapes are possible.

With reference more particularly to the embodiment of FIGS. 6 to 10, the two portions 11-1 and 11-2 of the oblong body 11 do not form a single part, but are constituted by two mutually separate parts 211 and 212.

In this configuration, and for a purpose that is explained below, it is possible and even advantageous for the cross-sections of the curved core 60, as defined in planes perpendicular to the curved axis 12, to present values that increase in substantially continuous manner starting from its first end 61 and going towards its free second end 62 that is remote from the first.

Nevertheless, although the above-described embodiment is often most advantageous, it is possible for the cross-sections of the curved core 60, as defined in planes perpendicular to the curved axis 12, to be substantially mutually identical.

It is stated above that the section of the curved core 60 should advantageously be polygonal. Nevertheless, it may be circular for example, in which case, and as can be seen more clearly in FIG. 10, it should be associated with at least one groove-and-rib pair, and preferably with two opposite pairs, each pair comprising a groove 91 formed in one of the following two elements: the curved core 60 and one of the portions 11-1 and 11-2 of the oblong body 11, and a rib 92 complementary to the groove 91 and made on the other one of the two elements, so that the rib 92 is suitable for sliding in the groove 91.

In FIG. 10, the groove 91 is made in one of the portions 11-1 and 11-2 of the oblong body 11, while the rib 92 is made on the curved core 60.

In advantageous manner, as in the embodiment shown in FIG. 10, the groove 91 and the rib 92 co-operate with a dovetail configuration in well-known manner. As mentioned above, the system includes a guide rod 50. As shown and more particularly visible in FIG. 11, the guide rod 50 is constituted by a hollow tube 55 and the pusher rod 80 is then slidably mounted in the hollow tube. The means 70 for mounting the first end 61 of the curved core 60 to co-operate with the first end 51 of the guide rod 50 are then constituted by fastener means for fastening the first end 61 of the curved core 60 on the wall of the hollow tube, and in continuity therewith.

The hollow tube 55 and the curved core 60 may be made as two separate parts that are secured to each other, or as a single part made from a single hollow tube. These embodiments come within the competence of the person skilled in the art and they are not described in greater detail herein, solely for the purpose of simplifying the present description.

The system of the invention in the two embodiments shown respectively in FIGS. 1 to 5 and in FIGS. 6 to 10 is used as follows.

In known manner, the practitioner begins by making an incision in the patient's back in order to create an introduction path that passes in particular between the two nerves of vital importance as is well known to practitioners.

First embodiment of the System, FIGS. 1 to 5 and 11

Figure 3:
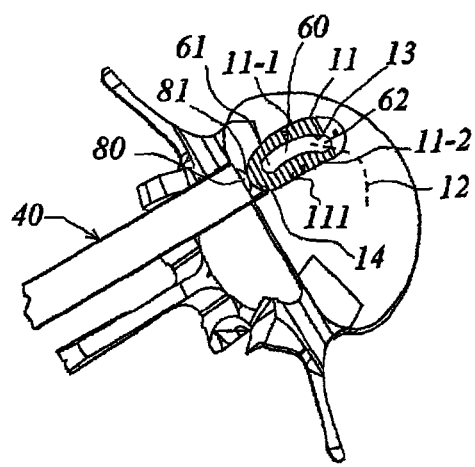
Figure 4:
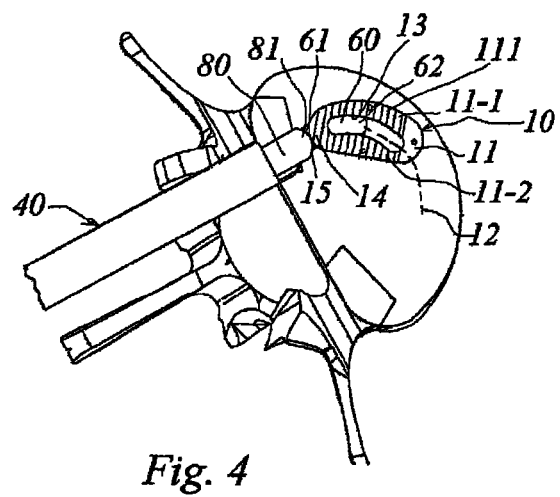
Figure 5:
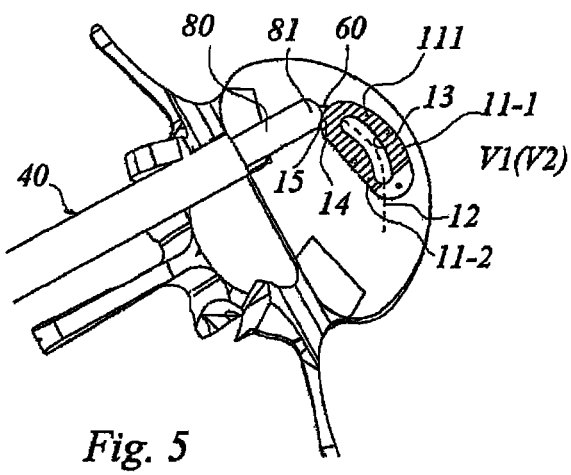

Via this incision, the practitioner introduces the introducer guide 40 with the curved core 60 already introduced in full in the hole 13 in the oblong body 11. In this way, the cage 10 is almost completely in continuity with the hollow tube 55, as shown in FIG. 3. This configuration makes it easy to introduce the cage 10 between the two vertebrae V1 and V2, while passing between the two nerves.

When the cage is positioned as shown in FIG. 3, the practitioner pushes the push rod 80 inside the hollow tube 55 so that its end 81 comes into contact with the end 14 of the oblong body 11. The practitioner continues to push on the push rod 80, and under the effect of this pushing the oblong body 11 moves relative to the curved core 60 along the curved axis 12 to its final position (FIG. 5), thereby replacing the intervertebral disk between the two vertebrae V1 and V2, i.e. by causing the cage to turn through about ninety degrees relative to its introduction direction.

When the cage 10 reaches its final position, the curved core 60 is completely outside the hole 13 and the introducer guide 40 can be withdrawn in the direction opposite to that used for introducing it.

Second embodiment of the System, FIGS. 6 to 10 and 11

Figure 6:
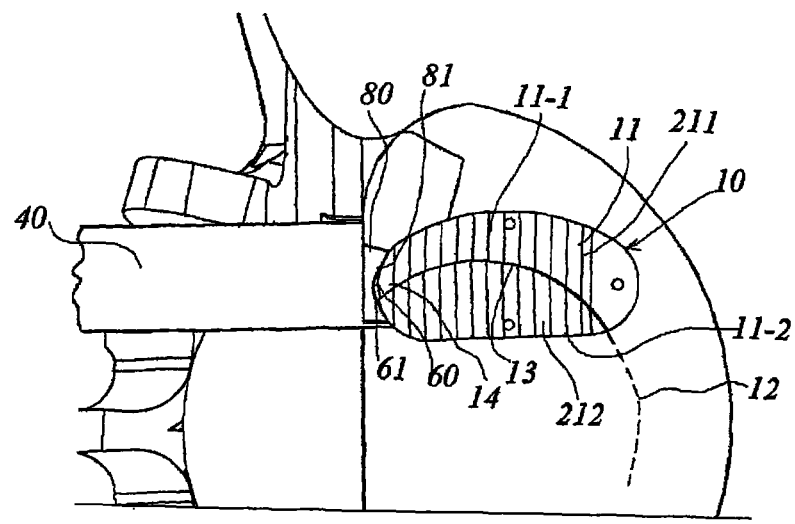
FIGS. 6 to 9 show various configurations of the FIG. 1 embodiment of the system in its use for implanting a cage having a structure that is other than that shown in FIGS. 1 to 5, FIG. 6 showing the system in its initial configuration, the cage already being interposed between the two vertebrae in an initial situation, FIGS. 7 and 8 showing the system respectively in two intermediate configurations, and FIG. 9 showing the system with the cage in its final situation.
Figure 7:
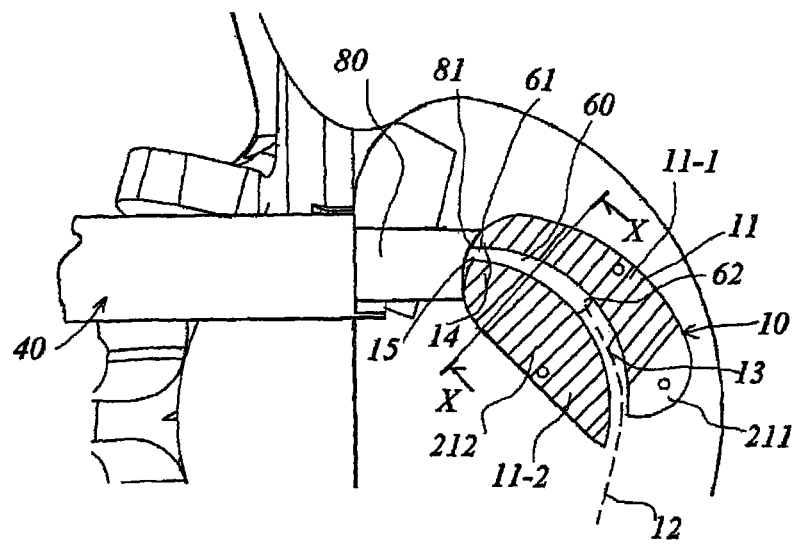
Figure 8:
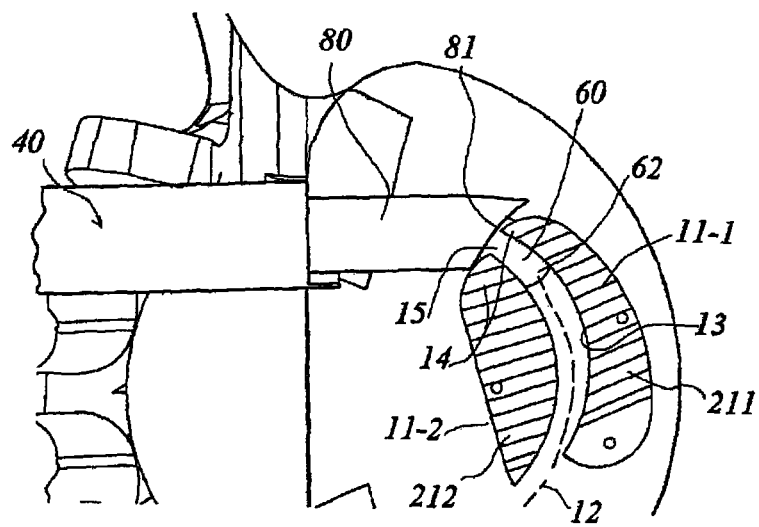
Figure 9:
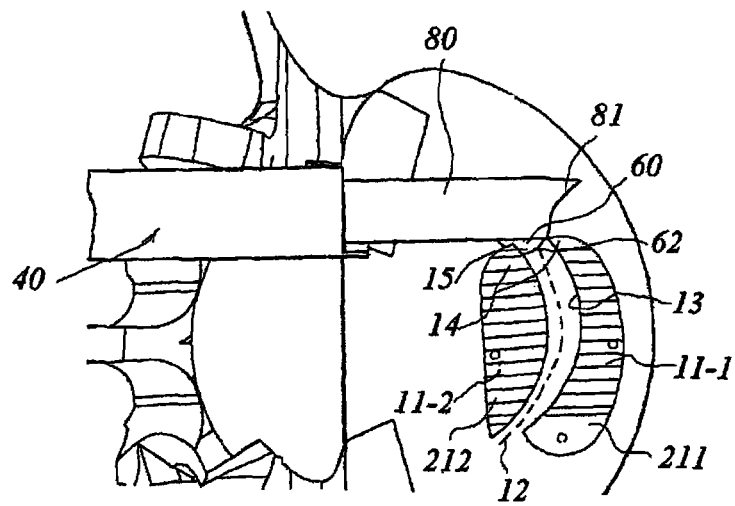

Using the above-described incision, the practitioner introduces the introducer guide 40 with the curved core 60 fully introduced in the hole 13 in the oblong body 11. In this way, the cage 10 is almost completely in continuity with the hollow tube 55, as shown in FIG. 6, and this configuration makes it easy to introduce the cage 10 between the two vertebrae V1 and V2 by passing between the two nerves and other vital organs.

Nevertheless, in this embodiment, since the oblong body 11 is made up of two mutually separate parts 211 and 212, they are mounted to co-operate in such a manner that the two ribs 92 formed on the curved core 60 are slidably mounted in the two grooves 91 formed respectively in the two parts 211 and 212. This ensures that the three elements constituted by the curved core 60 and the two parts 211 and 212 are properly held relative to one another.

The cage is positioned between the vertebrae V1 and V2 in the manner described above with reference to FIGS. 1 to 5 and 11 for the first embodiment of the system. Nevertheless, since the two parts 211 and 212 are separate from each other in this embodiment and since the sections of the curved core 60 increase in the manner defined above, by pushing on these two parts 211 and 212 relative to the curved core 60, as they move along they also move apart progressively from each other, as shown in the four FIGS. 6 to 9, until they reach their final position shown in FIG. 9.

This second embodiment makes it possible, so to speak, to position two mutually spaced apart half-cages 211 and 212 simultaneously so as to fill the intervertebral space better when replacing the original intervertebral disk, with it being possible to place in this space 13 a bone graft or the like, for example.

Naturally, it is also possible to use the system of the invention with a cage comprising two parts 211 and 212 that are separate from each other and a curved core 60 that is of uniform section along its entire length, i.e. that does not increase as in the embodiment described above.

The invention claimed is:

1. A system for replacing a disk between two consecutive vertebrae (V1, V2), the system comprising at least one intervertebral cage (10) and an introducer guide (40) for introducing said intervertebral cage between the two vertebrae, and being characterized by the facts that:
    the intervertebral cage (10) is constituted by an oblong body (11) defined between two substantially parallel opposite faces, said oblong body comprising at least two portions (11-1, 11-2) separated by a gap (13), said gap being defined along a curved axis (12) contained in a midplane substantially parallel to the planes of the opposite faces and opening out via an opening (15) at a first end (14) of the oblong body (11) between said two portions (11-1, 11-2) of said oblong body; and
    the introducer guide (40) is constituted by at least:
        a guide rod (50);
        a curved longitudinal core (60) of cross-sections that are substantially complementary to the cross-sections of said gap (13), so as to enable said curved core to slide relative to the two portions (11-1, 11-2) of said oblong body (11);
        means (70) for mounting a first end (61) of said curved core (60) to co-operate with a first end (51) of said guide rod (50) in such a manner that said curved core (60) projects from said first end (51) of said guide rod (50); and
        a push rod (80) mounted to move relative to said guide rod (50) in such a manner as to be suitable for coming into contact via one of its ends (81) against the first end (14) of the oblong body (11) in order to push said oblong body in translation relative to said curved core (60).

2. A system according to claim 1, characterized by the facts that said oblong body (11) is constituted by a single part (111) and that said gap (13) is constituted by a hole formed in said single part, substantially along said curved axis (12).

3. A system according to claim 1, characterized by the fact that the single part (111) is substantially in the shape of a kidney bean having opposite faces that are substantially plane.

4. A system according to claim 2, characterized by the fact that all of the cross-sections of said curved core (60), as defined in planes perpendicular to said curved axis (12), are substantially mutually identical.

5. A system according to claim 4, characterized by the fact that the cross-sections of said curved core (60), defined in planes perpendicular to said curved axis (12), are polygonal in shape.

6. A system according to claim 1, characterized by the fact that the two portions (11-1, 11-2) of said oblong body (11) are constituted by two mutually separate parts (211, 212).

7. A system according to claim 6, characterized by the fact that the cross-sections of said curved core (60), defined in planes perpendicular to said curved axis (12), are of values that increase substantially continuously from its first end (61) to its free second or other end (62) opposite from the first.

8. A system according to claim 6, characterized by the fact that all of the cross-sections of said curved core (60), as defined in planes perpendicular to said curved axis (12), are substantially mutually identical.

9. A system according to claim 1, characterized by the fact that it further includes at least one groove-and-rib pair comprising both a groove (91) formed in one of the following two elements: the curved core (60) and one of the portions (11-1, 11-2) of said oblong body (11), and also a rib (92) complementary to said groove (91), said rib being made on the other one of the two elements in such a manner that said rib (92) is suitable for sliding in said groove (91).

10. A system according to claim 9, characterized by the fact that said groove (91) and said rib (92) co-operate by dovetail mounting.

11. A system according to claim 1, characterized by the facts that said guide rod (50) is constituted by a hollow tube (55), that the push rod (80) is slidably mounted in said hollow tube, and that the means (70) for mounting the first end (61) of said curved core (60) in co-operation with the first end (51) of said guide rod (50) are constituted by fastener means for fastening the first end (61) of said curved core (60) on the wall of said hollow tube and in continuity therewith.

12. A system according to claim 3, characterized by the fact that all of the cross-sections of said curved core (60), as defined in planes perpendicular to said curved axis (12), are substantially mutually identical.

13. A system according to claim 12, characterized by the fact that the cross-sections of said curved core (60), defined in planes perpendicular to said curved axis (12), are polygonal in shape.

* * * * *